United States Patent
Langer et al.

(10) Patent No.: US 9,536,704 B2
(45) Date of Patent: Jan. 3, 2017

(54) METHOD FOR AVOIDING ARTEFACTS DURING SERIAL BLOCK FACE IMAGING

(71) Applicant: Carl Zeiss Microscopy GmbH, Jena (DE)

(72) Inventors: Matthias Langer, Heubach-Lautern (DE); Rainer Arnold, Ulm (DE); Markus Esseling, Aalen (DE); Jaroslaw Paluszynski, Oberkochen (DE)

(73) Assignee: Carl Zeiss Microscopy GmbH, Jena (DE)

( * ) Notice: Subject to any disclaimer, the term of this patent is extended or adjusted under 35 U.S.C. 154(b) by 421 days.

(21) Appl. No.: 14/021,075

(22) Filed: Sep. 9, 2013

(65) Prior Publication Data

US 2014/0092230 A1 Apr. 3, 2014

(30) Foreign Application Priority Data

Sep. 28, 2012 (DE) ........................ 10 2012 217 761

(51) Int. Cl.
*H01J 37/28* (2006.01)
*H04N 7/18* (2006.01)
(Continued)

(52) U.S. Cl.
CPC .......... *H01J 37/28* (2013.01); *G01N 23/2251* (2013.01); *H01J 37/222* (2013.01); *H04N 7/18* (2013.01);
(Continued)

(58) Field of Classification Search
None
See application file for complete search history.

(56) References Cited

U.S. PATENT DOCUMENTS

| 4,377,958 A | 3/1983 | Leighton |
| 8,227,752 B1 | 7/2012 | Mantz et al. |

(Continued)

FOREIGN PATENT DOCUMENTS

| DE | 10 2008 040 426 | 2/2010 |
| EP | 2009 421 | 7/2009 |
| EP | 2 383 768 | 11/2011 |

OTHER PUBLICATIONS

Denk et al., "Serial Block-Face Scanning Electron Microscopy to Reconstruct Three-Dimensional Tissue Nanostructure", PLoS biology, vol. 2, Issue 11, Nov. 2004.*
(Continued)

*Primary Examiner* — Michael Logie
(74) *Attorney, Agent, or Firm* — Fish & Richardson P.C.

(57) ABSTRACT

A method includes capturing a first image of the sample via a detector, wherein the particles of the primary particle beam have a first average energy so that the interaction products detected by the detector predominantly contain sample information from a sample layer lying below the sample surface. The method also includes removing the outermost sample layer with the aid of the cutting device, and capturing a second image of the sample via the detector, wherein the particles of the primary particle beam have a second average energy so that the interaction products detected by the detector predominantly contain sample information from the surface layer of the sample. The method further includes calculating the lateral shift/lateral offset of the sample from a comparison of the first and second images, and compensating for the lateral offset.

24 Claims, 9 Drawing Sheets

(51) Int. Cl.
*G01N 23/225* (2006.01)
*H01J 37/22* (2006.01)

(52) U.S. Cl.
CPC ... *G01N 2223/401* (2013.01); *G01N 2223/418* (2013.01); *H01J 2237/221* (2013.01); *H01J 2237/226* (2013.01)

(56) References Cited

U.S. PATENT DOCUMENTS

| | | | | |
|---|---|---|---|---|
| 8,431,896 | B2* | 4/2013 | Mulders | G01N 1/30 250/307 |
| 8,481,933 | B2* | 7/2013 | Albiez | G01N 23/2251 250/306 |
| 2009/0000400 | A1* | 1/2009 | Hayles | G01N 1/06 73/863.12 |
| 2001/0102223 | | 4/2010 | Albiez et al. | |
| 2010/0102223 | A1* | 4/2010 | Albiez | G01N 23/2251 250/307 |
| 2012/0223228 | A1* | 9/2012 | Galloway | G01N 1/06 250/310 |
| 2013/0037714 | A1* | 2/2013 | Boughorbel | H01J 37/222 250/307 |
| 2013/0094716 | A1* | 4/2013 | Carpio | G06T 5/50 382/109 |
| 2013/0228683 | A1* | 9/2013 | Boughorbel | H01J 37/222 250/307 |
| 2014/0226003 | A1* | 8/2014 | Phaneuf | H01J 37/222 348/80 |
| 2014/0312226 | A1* | 10/2014 | Boughorbel | H01J 37/222 250/307 |

OTHER PUBLICATIONS

Denk et al., "Serial Block-Face—Scanning Electron Miscroscopy to Reconstruct Three-Dimensional Tissue Nanostructure," PLoS Biology, vol. 2 (11), e329, pp. 1-10, 2004.

Al-Amoudi et al., "An oscillating cryo-knife refudes cutting-induced deformation of vitreous ultrathin sections," Journal of Microscopy, vol. 212, Oct. 2003, pp. 26-33.

German Office Action, with translation thereof, for corresponding DE Appl. No. 10 2012 217 761.2, dated Jul. 17, 2013.

* cited by examiner

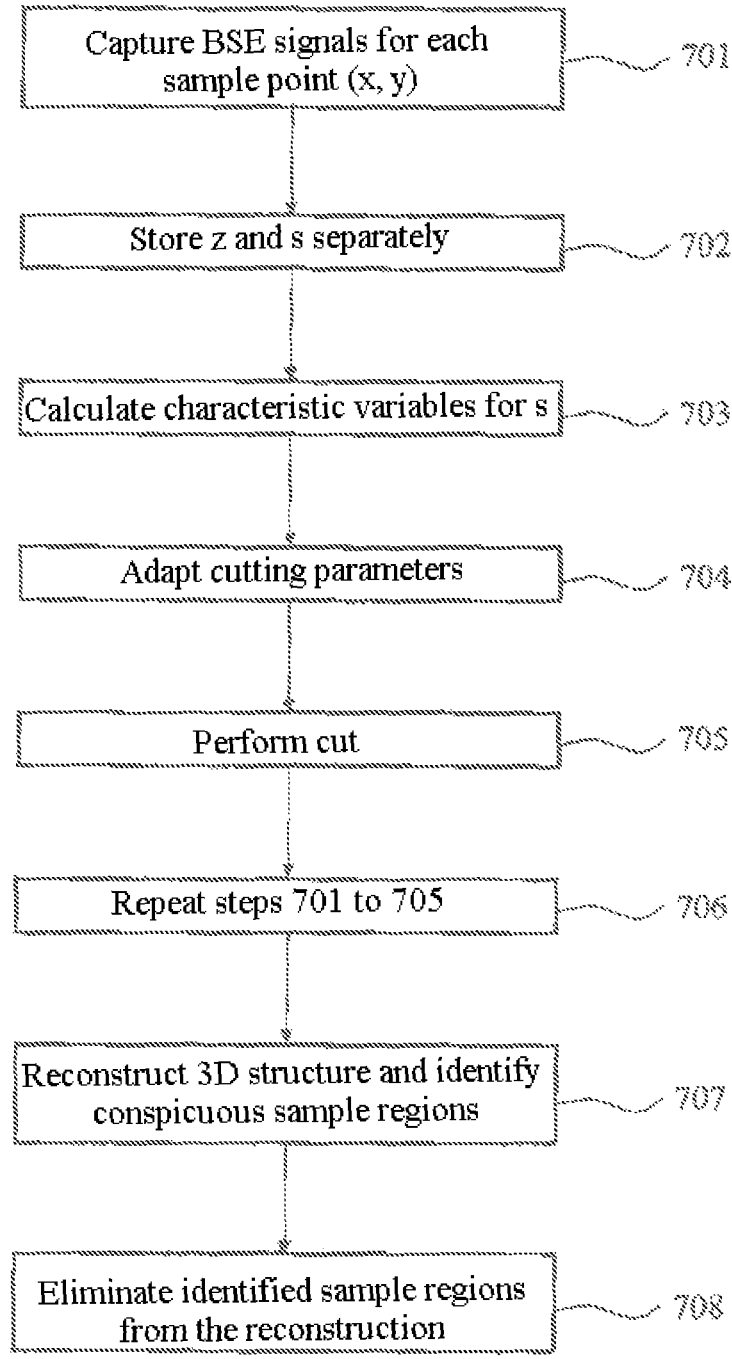

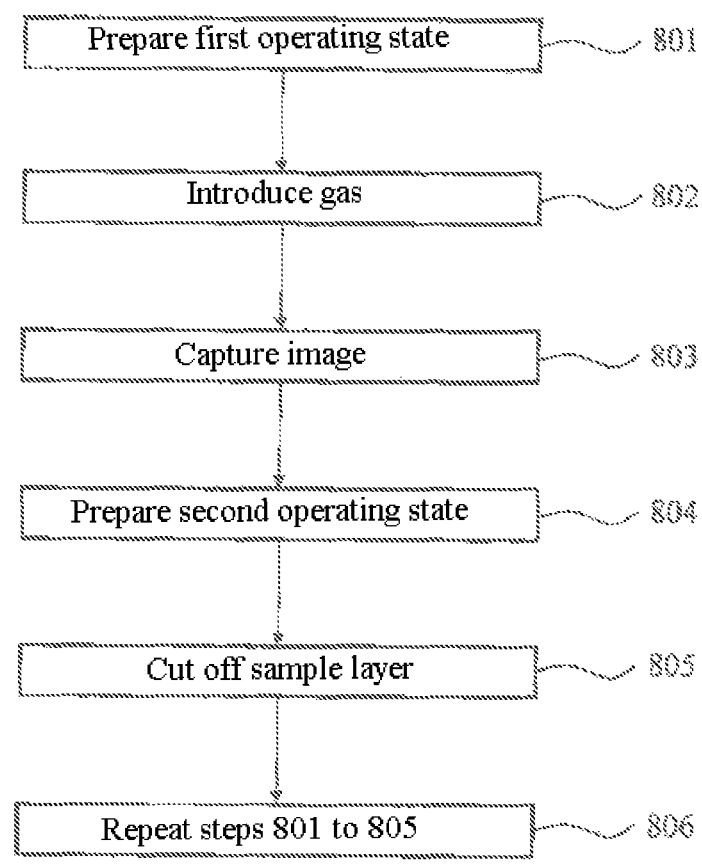

METHOD FOR AVOIDING ARTEFACTS DURING SERIAL BLOCK FACE IMAGING

The invention relates to methods for identifying and compensating for and/or avoiding artifacts which can occur during serial block face imaging.

Serial block face imaging is a known method which allows a three-dimensional reconstruction (3D reconstruction) of a sample to be produced. For this purpose, the sample material is brought to the form of a block and an image of a surface of the block (block face) is generated and stored. The outermost sample layer, which was imaged, is then removed. As a result, a next sample layer is uncovered, which is now the outermost sample layer. An image of this new sample surface is generated and stored. Afterwards, this sample layer in turn is removed, an image of the newly uncovered sample surface is captured and stored, and the next sample layer is again removed, and so on, until a series of images has been created and stored, on the basis of which a 3D reconstruction of the sample block can be created computationally.

Serial block face imaging can be performed with the aid of a particle-optical apparatus, for example a scanning electron microscope (SEM), in the sample chamber of which is situated an ultramicrotome having a microtome blade. The sample surface is imaged by the SEM. Afterwards, the respective outermost sample layer is repeatedly cut off by the ultramicrotome and the sample layer thereby uncovered is imaged by the SEM. In the case of a series of images produced in this way, various types of artifacts are known which adversely influence the generated images of the sample and the quality of the 3D reconstruction.

Artifacts are undesirable alterations of the sample which can arise inadvertently when the sample is prepared, that is to say prepared for the actual examination, but also when the sample is imaged. That has the effect that images obtained from such a sample be set by artifacts no longer reproduce the native state of the sample details, and the meaningfulness of these images is thus greatly restricted. Therefore, it is advantageous to identify artifacts and to prevent them from arising.

In serial block face imaging, which is performed using a particle-optical apparatus with an ultramicrotome, various types of artifacts can occur.

In this regard, sample details such as, for example, cell structures and biological samples can be deformed on account of the mechanical action during cutting. As a result of the lateral force action of the cutting blade, the sample block can be laterally shifted or deformed, even if the sample block is sufficiently secured on the sample holder. The 3D reconstruction created from such a sample is impaired by horizontal distortions.

Moreover, the sample surface (block face) to be imaged can be deformed by the cut of the microtome blade, with the result that a ripple-like surface profile of the cut parallel to the edge of the blade, also called "chatter", can occur. It is also possible for longitudinal striations running perpendicular to the edge of the blade to occur. The 3D reconstruction based on images of such sample surfaces then contains erroneous image information on account of the high degree of surface roughness of the sample. In the extreme case, the surface of the sample block may even have been cut off in a step-like manner. Such a surface topography of the sample can lead to a falsification of the 3D reconstruction because items of image information which originate from sample layers at different depths are combined in an image plane of the reconstructed entity.

Similar artifacts can occur if the cut was not guided perfectly, which means that the sample material was not separated with a smooth cut, rather unseparated sample residues remain on the sample surface. A sample structure that was not present in the original sample can be simulated as a result.

If the microtome blade is not oriented exactly at right angles relative to the optical axis of the particle-optical apparatus, the sample is cut off obliquely. That means that the sample surface is not exactly at a right angle relative to the optical axis of the SEM and, therefore, the primary particle beam impinging on the sample and the sample surface form an angle relative to one another that deviates from 90°. In the case of such inadvertent sample inclination, there will always be sample regions which are not in the focus and can therefore only be imaged unsharply.

Biological samples are generally embedded into resin-like substances in order to form a solid sample block. Since natural or synthetic resins are not electrically conductive or have only poor electrical conductivity, the sample surface is charged when the primary particle beam impinges on the sample and the electrical charges transferred in this case cannot be dissipated. This can lead to charging-governed signal amplification that simulates a structure not present. Moreover, undesirable image drift can occur.

BRIEF DESCRIPTION OF THE RELATED PRIOR ART

An automated method of serial block face imaging is known which captures the series of cuts with the aid of a miniaturized ultramicrotome situated in the vacuum chamber of a scanning electron microscope. The series of images is captured by a BSE detector. In this case, the SEM is operated under low-vacuum conditions in order to prevent the sample surface from being charged.

Moreover, a method has been described in which undesirable charges on the sample face are locally compensated for by introducing inert gas.

Furthermore, it has been proposed to use an oscillating microtome blade, which is intended to reduce cut-governed sample deformations. In order to assess the quality of the proposed method, the extent of sample deformation is determined by spherical objects being imaged microscopically; in the two-dimensional representation, these objects—depending on the degree of cut-governed deformation—then appear circular or elliptic.

Another possibility is to entirely dispense with the use of a microtome and to remove the sample layers by milling, that is to say by ion beam figuring. What is disadvantageous about the last-mentioned method is that it is very time-consuming and ions are implanted into the sample material.

The following documents should be regarded as prior art
U.S. Pat. No. 4,377,958
EP 2009 421
DE 10 2008 040 426
Denk, W. & Horstmann, H. (2004), PLoS Biology, Vol. 2 (11), e329, pp. 1-10
Al-Amoudi et al. (2003); Journal of Microscopy, Vol. 212, pp. 26-33

OVERVIEW OF THE INVENTION

The problem addressed by the present invention is that of proposing an automated process by which artifacts which can occur during block face imaging performed via a particle-optical apparatus with an ultramicrotome can be identified, prevented or compensated for.

This problem is solved according to the invention via a method comprising the features of Claim 1. Advantageous configurations of the invention are provided by the dependent claims.

In order to perform the method according to the invention, a block-shaped sample is required which is constituted such that it can be examined in a particle-optical apparatus. For this purpose, the sample is prepared depending on the respective sample material, i.e. for example fixed and—if necessary—stained as a whole, and finally embedded into a suitable embedding agent. The embedding agent is usually a resin, for example a natural or synthetic standard resin for electron microscopy, which has usually been modified such that it is opaque.

The embedded sample is then trimmed, i.e. cut, so as to give rise to a block shape, preferably a parallelepipedal or pyramidal shape, preferably having a trapezoidal base surface. The sample block is taken up by a sample holder, such that the sample holder with the sample block can be introduced into the vacuum chamber of a particle-optical apparatus. The sample blocks having a side length of a few millimeters are usually used. The sample block is mounted in the vacuum chamber in such a way that it is movable. For this purpose, the particle-optical apparatus comprises a movable sample stage, on which the sample block is held. Via the sample stage, the sample can be moved along different axes, preferably along the x-axis, y-axis, z-axis, rotational axis and tilting axis. It is advantageous if the sample stage can be moved via a computer control.

The particle-optical apparatus into which the sample block is introduced can be a scanning electron microscope (SEM), or a two-beam apparatus, i.e. a combination apparatus comprising SEM and ion microscope having a focussed ion beam (FIB). The particle-optical apparatus comprises at least one particle source, which can be an electron source or an ion source. The particle source generates a primary particle beam that is directed on to the sample, wherein the particles of the primary particle beam are accelerated by an acceleration voltage being applied. The particles of the primary particle beam are subjected to a defined acceleration voltage, such that the particles have a defined average energy. The acceleration voltage can be variable, such that the average energy of the particles can also be varied. The primary particle beam is guided over the sample surface preferably in a raster-like manner within a scanning field usually embodied as a rectangle. It is advantageous if the primary particle beam can be deflected (beam shift) such that the scanned scanning field can be laterally shifted in a targeted manner. The particles of the primary particle beam which impinge on the sample interact with the sample material, such that interaction products are released from the sample. The particle-optical apparatus comprises at least one detector which can detect these interaction products in order to generate therefrom an image of the sample surface (block face) impinged on by the primary particle beam. A BSE detector and/or an SE detector are/is usually used for detecting the interaction products, depending on whether the intention is to use backscattered electrons (BSE) and/or secondary electrons (SE) for image generation. It is also conceivable to detect interaction products using other suitable detectors.

After an image of the surface of the sample block has been captured and stored, the surface layer that has just been imaged is removed. For this purpose, the particle-optical apparatus comprises a miniaturized microtome situated within the sample chamber. The microtome can be an ultramicrotome. The microtome comprises a microtome blade, preferably a diamond blade, via which the surface of the sample block can be cut off. It is advantageous if the blade is designed such that it can oscillate during the cutting process. The quality of the cut can be influenced by the oscillation movement, the frequency and amplitude of which are preferably variable. The sample layers cut off are discarded. The removal of the surface layer uncovers a next sample region, which now forms the surface of the sample block. An image of this new sample surface is then captured and stored. Subsequently, in the manner described, the next sample layer is removed, an image of the sample surface newly arisen is captured and stored, then once again the next sample layer is removed, and so on, until a series of images has been captured and stored. On the basis of the stored series of images, a 3D reconstruction of the sample block can be created with the aid of a suitable computing unit and a corresponding computer program.

A method according to the present invention relates to identifying and compensating for lateral shifts of the sample, caused by the lateral force action of the cutting microtome blade during the block face imaging process. The method according to the invention makes use of the fact that image information from sample layers at different depths can be represented depending on the chosen acceleration voltage of the primary particle beam; in this way, two images of the same sample layer can be captured, wherein the first image is captured as long as this sample layer still lies within the sample block. The second image is captured after a sample layer situated further on the outer side has been removed and, in this way, the sample layer imaged in the first image has been uncovered as a new surface layer. This new surface layer is imaged in the second image. A lateral offset can be identified by comparing the first and second images.

In the method according to the invention, a first step involves capturing an image of the sample block by detecting interaction products that arose on account of the interaction of primary particles of a primary particle beam with the sample material. For this purpose, the particles of the primary particle beam are accelerated by a first acceleration voltage (EHT1) being applied. This first acceleration voltage has the effect that the particles of the primary particle beam have a first average energy. The first acceleration voltage—and thus also the first average energy of the primary particles—is chosen such that the detectable interaction products predominantly yield sample information from a sample layer lying below the sample surface. In one specific embodiment of the invention, by way of example, an acceleration voltage of 2 kV can be applied, which leads to an average energy of the primary particles of 2 keV and yields image information from a depth of approximately 20 nm. The interaction products that arose are detected with the aid of a suitable detector, for example a BSE detector. A first image of the sample is generated from the detected signals.

A second step involves removing the outermost sample layer via an ultramicrotome cut. In this case, the outermost sample layer is removed precisely with the thickness such that that sample layer from which the sample information originated in the preceding method step, i.e. which was imaged, reaches the surface of the sample block. Usually, the removed sample layer has a thickness of between 10 nm and 50 nm, for example 20 nm.

A second acceleration voltage (EHT2)—and thus a second average energy of the primary particle beam—is then chosen in such a way that the sample information obtained originates from the newly uncovered sample surface. The released interaction products are detected with the aid of the detector, and a second image is generated.

By comparing the first and second images of the sample it can be identified whether the imaged sample details have been laterally shifted during the cutting process. If such a lateral offset can be identified, the extent of the lateral offset can be determined, such that the offset can be compensated for computationally during the subsequent 3D reconstruction. The extent of the offset can be determined by computational methods, for example by applying the cross-correlation function. Additionally or alternatively, during the subsequent capture of further images of a series of images, the sample stage and/or the particle beam can be moved before each cutting process in such a way that the offset to be expected during the cutting process is compensated for.

In one specific embodiment, during the capture of a series of images in the course of serial block face imaging, the method according to the invention is performed each time a sample layer is severed. In another advantageous embodiment, the method according to the invention is not performed after each occasion when a sample layer is severed, but rather only after a specific number of cutting processes, for example after every 50th or every 100th cutting process or—depending on the conditions—after any other number of cutting processes.

In one specific embodiment of the method according to the invention, it is furthermore possible to determine and, if necessary, to correct the angle at which the primary particle beam impinges on the sample. For this purpose, a series of images is captured, wherein the focal planes of the individual images of the series of images differ from one another: each time an image is captured, the focal plane is altered, and so the focal plane is in each case different from all preceding focal planes. All the images are stored and used for calculating a 3D reconstruction of the sample block. The angle at which the primary particle beam impinges on the sample surface can be determined on the basis of the 3D reconstruction. Further details regarding the method are described in U.S. Pat. No. 8,227,752.

In a further, alternative embodiment, SE signals from, for example, three sample regions are captured, wherein these regions together span an imaginary area which lies in the sample surface scanned by the primary particle beam. The detected signals from each of these regions are subjected to a frequency-based computational algorithm. The result of the calculation allows conclusions to be drawn about whether the respective sample region is in the focus and—in the overall consideration of the sample regions analyzed—whether the sample surface is tilted in relation to the optical axis.

In a further specific embodiment of the method according to the invention, it is additionally possible to identify a cut not guided exactly. In the case of a cut not guided exactly, the microtome blade has not severed the sample material from the sample block in a smooth cut. Rather, sample regions not severed have inadvertently remained on the sample surface, and so a non-natural sample topography is simulated.

In one specific embodiment of the method according to the invention, in addition to the BSE image of the sample, an SE image of the sample is captured with the aid of an in-lens detector. At edge-shaped structures or at locations at which sample material projects from the sample face, interaction products naturally emerge from the sample material to an increased extent, and can be detected with the aid of the SE detector. This effect is known from the literature as the edge effect. In the method according to the invention, the edge effect has the consequence that, at those sample locations at which edge-shaped structures or projecting sample material are/is present, the detected SE signal is overdriven or approximately overdriven and can thus be differentiated from other sample locations. If a cut not guided exactly in the series of cuts captured in the course of the serial block face imaging has been identified in this way, the delivery of the microtome blade, in other words cutting speed and/or oscillation frequency and/or oscillation amplitude of the microtome blade, can be correspondingly adapted for the following cuts of the series of cuts. Moreover, it is possible to assign these sample locations to the corresponding image data with the aid of their spatial coordinates, such that sample information from these sample locations can be excluded from the 3D reconstruction of the sample block on the basis of the simultaneously captured BSE series of images.

In a further embodiment of the method according to the invention, the surface roughness of the sample surface is determined. The surface roughness is a measure of the texture of a sample surface. The vertical deviation of a specific surface from an ideal surface is usually used for quantifying the surface roughness. For this purpose, the surface to be examined is compared with the ideal surface. In this case, it is customary, for the purpose of quantifying the surface roughness, to compare only the profile line of the surface to be examined with the profile line of the ideal surface, in order in this way to determine the vertical deviation of the profile line to be examined from the ideal profile line. In the method according to the invention, the height information (topography) can be detected for each point of the sample surface and stored. The surface roughness is calculated on the basis of these data. On the basis of the results obtained, the cutting parameters of the subsequent cutting processes are adapted such that the surface roughness of the sample surfaces produced during the subsequent cutting is reduced.

In one extension of the method according to the invention, it is additionally possible to compensate for undesirable charging by neutralizing the sample surface via local ionization of gases brought about in a targeted manner in the vicinity of the charging locations.

EXEMPLARY EMBODIMENTS

Exemplary embodiments of the invention are explained below with reference to figures. In this case, components which correspond to one another with regard to their structure and function are provided with reference signs which have the same numerals that are supplemented by an additional letter for differentiation purposes.

FIG. 1 schematically shows an apparatus suitable for performing the method according to the invention.

FIGS. 5 to 7 show flowcharts of further specific embodiments of the method according to the invention.

FIG. 8 shows an extension of the method according to the invention.

Figure 1:
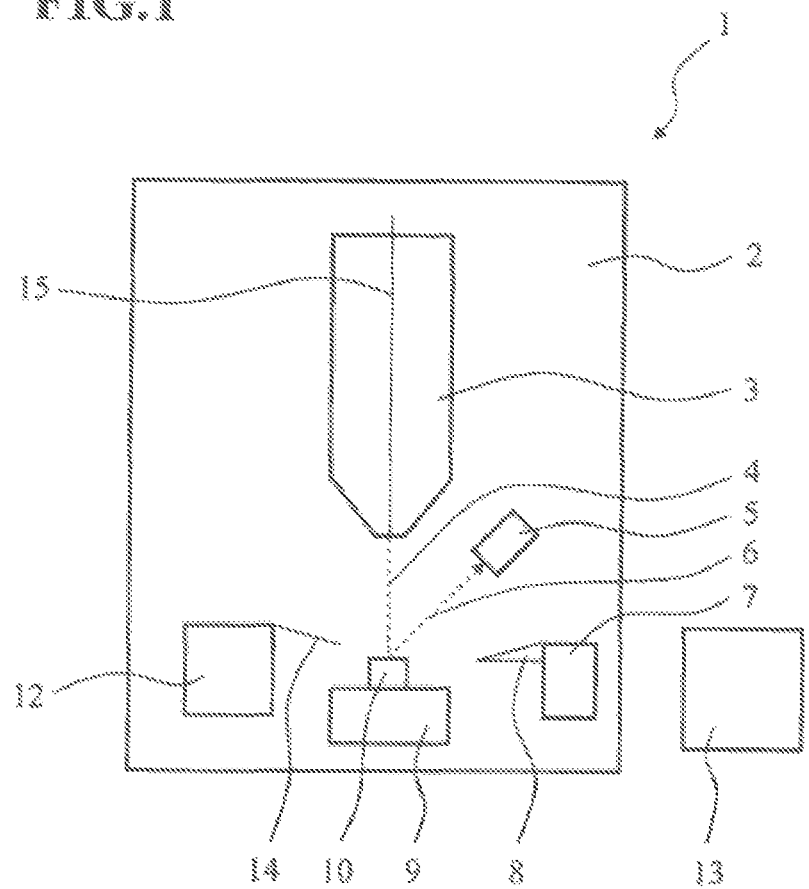

FIG. 1 shows an apparatus suitable for performing the method according to the invention. The apparatus comprises a particle-optical apparatus 1, which can be designed as an electron beam apparatus, for example as a scanning electron microscope. The electron beam apparatus has a particle source (not illustrated), which is situated in an electron-optical column 3 and generates primary particle beams 4. The primary particle beams 4 run parallel to the optical axis 15 of the particle-optical apparatus 1. The primary particle beams 4 are directed onto the sample block 10 and are guided over the sample in a raster-type manner, wherein the scanned scanning field preferably has a rectangular form. It is advantageous, moreover, if the primary particle beam 4 can be laterally shifted (beam shift). This should be understood to mean that the primary particle beam 4 is deflected laterally in a particular way, such that the scanning field to be scanned is shifted to a different location of the sample. The sample block 10 is situated on a movable sample stage 9 within a sample chamber 2, which is designed to accommodate a sample and in which vacuum conditions prevail. The sample stage 9 is designed such that it is movable in a plurality of directions, preferably in the x-, y-, z-directions. Moreover, the sample stage 9 is rotatable about at least one tilting axis, preferably about two tilting axes that are orthogonal to one another, and is rotatable about a rotation axis. Moreover, a cutting device 7 designed as a microtome 7, which comprises a microtome blade 8, is situated within the sample chamber 2. The microtome 7 is preferably designed to be movable, for example by virtue of the fact that the microtome 7 is designed as a movable unit or is arranged on a pivotable arm. With the aid of the microtome blade 8, material can be severed from the sample block 9 layer by layer. The movements both of the sample stage 9 and of the microtome blade 8 are controlled via an evaluation and control unit 13 and can be coordinated with one another. The microtome blade 8 can have a diamond cutting edge. In one specific embodiment, the microtome blade 8 is designed such that it oscillates during the cutting process. The frequency and amplitude of the blade oscillation are adjustable. The particles of the primary particle beam 4 impinge on the sample block 10, such that interaction products 6 are released on account of the interaction between the impinging particles and the sample material, the interaction products being detected by at least one first detector 5. From the signals detected by the first detector 5, an image of the sample is generated via an evaluation and control unit 13. In this case, it is possible to allocate a pixel having the coordinates x and y to each sample point and to store it.

In one advantageous embodiment, the particle-optical apparatus 1 additionally comprises a second detector (not depicted), which can be an SE detector. It is particularly advantageous if this detector is designed as an in-lens detector, which means that the detector is arranged within the electron-optical column 3.

In a further advantageous embodiment, the apparatus suitable for the method comprises a movable gas introducing apparatus 12 comprising a needle 14, which can be designed as a gas canula and via which gaseous substances can be directed to the sample surface.

With reference to FIG. 1, the invention is explained for the case where the particle-optical apparatus with which the invention can be performed is an electron beam apparatus. However, the invention can also be performed if the particle-optical apparatus is an ion beam apparatus or a two-beam microscope, that is to say a combination apparatus comprising an electron beam apparatus and an ion beam apparatus. A two-beam microscope has two beam sources which generate primary particle beams 4, to be precise an electron source, which is situated in an electron-optical column and which can generate an electron beam, and an ion source, which is situated in an ion-optical column and which can generate an ion beam. Ion beam apparatuses and electron beam apparatuses are constructed similarly, in principle. However—in contrast to electron beam apparatuses—ion beam apparatuses have an ion source instead of an electron source and only electrostatic lenses instead of magnetic lenses or combined electrostatic-magnetic lenses. Moreover, depending on the polarity of the ions, it is necessary, of course, also to correspondingly adapt the polarities of the potentials and potential differences applied to the different components.

Figure 2:
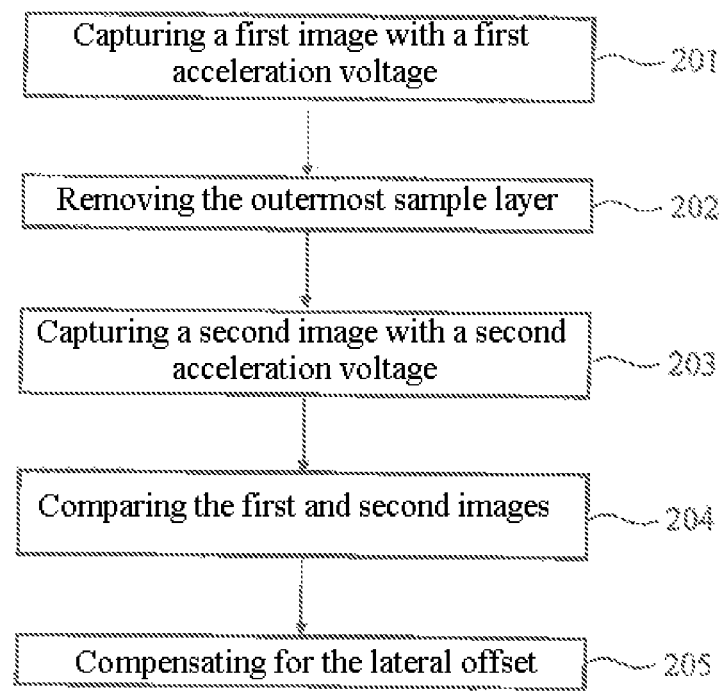
FIG. 2 shows a flowchart of the method according to the invention.

FIG. 2 shows a flowchart of a method according to the invention. The sample block of which a 3D reconstruction is intended to be created via serial block face imaging is situated in the sample chamber of the particle-optical apparatus. Step 201 involves capturing a first image of the sample block with a known magnification and with a first acceleration voltage. Depending on the first acceleration voltage, the particles of the primary particle beam have a first average energy chosen such that a sample layer lying below the sample surface in the sample block is imaged. In the subsequent step 202, the outermost layer of the sample block, which has hitherto covered the sample layer already imaged, is completely removed with the aid of the cutting device. Step 203 then involves capturing a second image of the sample block with a second acceleration voltage, i.e. with a second average energy of the particles of the primary particle beam, wherein the sample surface now newly formed is imaged with unchanged magnification. That means, therefore, that the first image and the second image effect imaging of the same or approximately the same sample layer and thus contain the same or approximately the same sample details. Step 204 involves comparing the first image and the second image with one another. If no lateral shift whatsoever occurred during the cutting process, both images are identical. However, if an offset can be identified upon comparison of the two images, this indicates that the sample was laterally shifted. This lateral offset is compensated for in step 205. This can be done by computational methods or by correspondingly moving the sample stage and/or shifting the primary particle beam during the capture of the series of images.

Figure 3A:
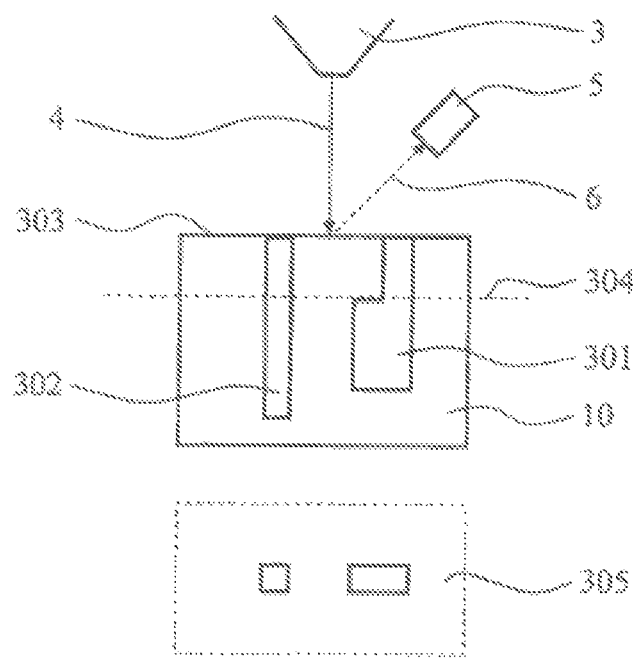
FIGS. 3a to 3c show by way of example one embodiment of the method according to the invention.

In order to clarify the method illustrated as a flowchart in FIG. 2, FIG. 3 illustrates steps 201 to 203 again on the basis of an example. FIG. 3a schematically illustrates the side view of a parallelepipedal sample block 10 in the upper part, and in the lower part in plan view an image 305 of the sample block 10 which was generated in the course of the block face imaging. A first sample detail 301 and a second sample detail 302 are situated within the sample block 10, these sample details being illustrated schematically. In the electron-optical column 3 of the particle-optical apparatus, a primary particle beam 4 is generated and subjected to an acceleration voltage in such a way that the primary particle beam 4 impinges on the first sample surface 303 (block face). On account of the interaction between the material of the sample block 10 and the accelerated particles of the primary particle beam 4, interaction products 6 arise and can be detected by a first detector 5. The detector 5 can be a BSE detector, for example, which detects backscattered electrons (BSE). The acceleration voltage is chosen such that the interaction products 6 detected by the detector 5 predominantly contain sample information from a sample layer 304 lying below the first sample surface 303. In order to obtain sample information from sample layers lying deeper than 20 nm below the sample surface, the acceleration voltage can be increased. The achievable penetration depth is greatly dependent on the nature of the sample material, in particular on the density thereof and the atomic number (Z) thereof. The higher the density and the higher the atomic number of a material, the smaller, generally, the penetration depth of the primary particle beam. The first image of the sample usually contains information from a sample layer lying 10 nm to 50 nm below the sample surface. A first image of the sample 305 is generated from the detected signals, the first image thus representing an image of the sample layer 304 lying within the sample block 10.

Figure 3B:
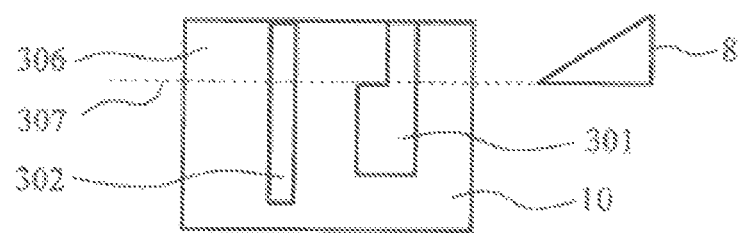

FIG. 3b shows how a cut is guided through the sample block 10 via the microtome blade 8 at the previously imaged sample layer 304, such that the outermost sample layer 306 is removed. The cut is guided along a desired cutting line of the microtome cut 307. It should be noted that, on account of the two-dimensional representation in FIG. 3b, a cutting line 307 is illustrated, but the latter represents a cutting area—since a three-dimensional sample block is involved. The cutting line of the microtome cut 307 is chosen such that the sample layer imaged in the preceding method step is uncovered and now forms the second sample surface 303a of the sample block 10.

Figure 3C:
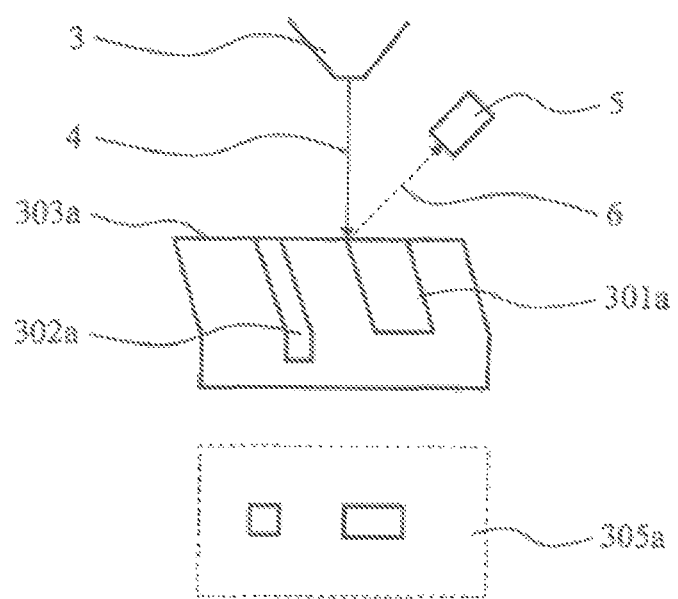

FIG. 3c schematically shows in the upper part the side view of the parallelepipedal sample block 10 after the outermost sample layer has been cut off. A second image of the sample, captured after cutting, is illustrated in plan view in the lower part of FIG. 3c. The sample block and the sample details 301a and 302a lying within it have been shifted laterally during the cutting process by the lateral force action of the microtome blade 8. The primary particle beam 4 generated in the electron-optical column 3 of the particle-optical apparatus is now subjected to a second acceleration voltage. The second acceleration voltage is chosen such that the interaction products 6 detected by the detector 5 predominantly contain sample information originating from the second sample surface 303a of the sample block 10 that has been newly formed by the cutting process.

It has proved to be advantageous if the first average energy of the primary particle beam 4 is greater than the second average energy of the primary particle beam 4. It is particularly advantageous if the acceleration voltages are chosen such that the first average energy of the primary particle beam 4 is greater than 2 keV and the second average energy of the primary particle beam 4 is less than 2 keV.

A second image of the sample 305a is generated from the detected signals, the second image representing the second sample surface 303a that has been newly formed. By comparing the two images 305 and 305a it becomes clear that the sample details 301 and 302 imaged in the first image 305 are shifted relative to the sample details 301a and 302a imaged in the second image 305a. In one specific embodiment, the comparison of the first image 305 and of the second image 305a is carried out by applying a cross-correlation function. The application of the cross-correlation function directly yields a statement about the extent of the shift of the sample details imaged in the two images, specified in pixels. On the basis of the magnification with which the two images have been captured, and which is known, it is possible to convert the shift into a length indication.

During the capture of images for the series of images, the sample is now moved with the aid of the movable sample stage in such a way that lateral shifts are compensated for. Alternatively, the primary particle beam can be deflected during the capture of the series of images in such a way that lateral shifts of the sample can be compensated for by shifting the scanned scanning field. Moreover, the lateral shifts of the sample can be compensated for by computational methods during the 3D reconstruction after a series of images has been captured.

In order to achieve optimum results with the method described, it should preferably be performed with specific parameter settings. There is a relationship between the chosen magnification and DOF (depth of film) and FOV (field of view), since DOF and FOV decrease as the magnification increases. DOF is understood to mean that path segment which runs along the optical axis of the particle-optical apparatus and in which an object must be situated in order that it can be imaged in a focussed manner. FOV is understood to mean that region of the sample which can be scanned by the primary particle beam and detected by a detector. The relationship between aperture angle $\alpha$, DOF and magnification Mag can be described as follows:

$$DOF = \text{line spacing of the display}/(Mag * \tan \alpha)$$

The line spacing on the display used for representing the image can be 200 µm, for example. For the method according to the invention it has proved to be advantageous to use a small magnification, for example 1000 times to 2000 times, and a large aperture angle $\alpha$ of the primary particle beam, for example of $\alpha = 5*10^{-2}$, in order to obtain a high resolution in the z-direction. It is advantageous if the method is performed with the aid of structure details on the sample surface which are at least 5 to 10 times larger than the current DOF value.

The method according to the invention is additionally suitable for identifying shrinkage of the sample material caused by the influence of the primary particle beam. If shrinkage artifacts occur, the dose of the primary particles impinging on the sample should be reduced.

Figure 4:
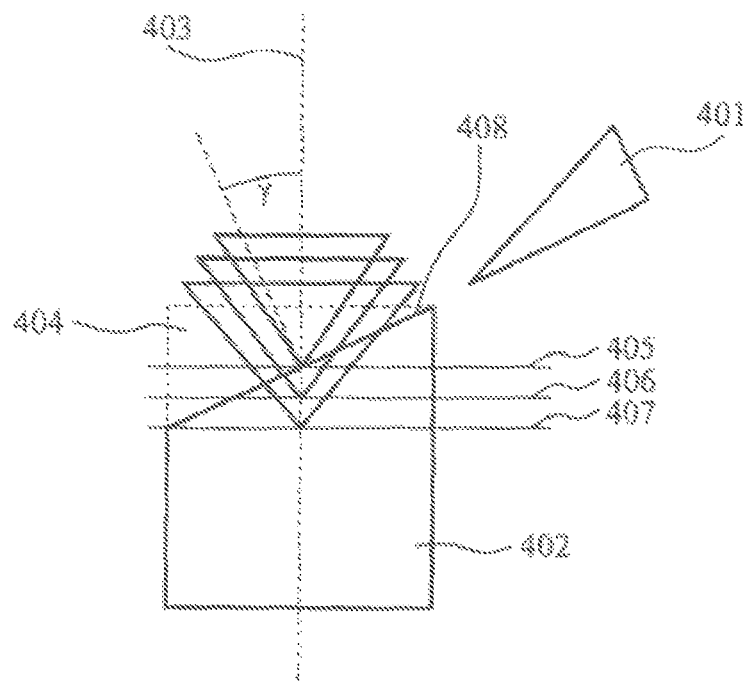
FIG. 4 shows by way of example a further advantageous embodiment.

FIG. 4 shows by way of example a further advantageous embodiment of the invention. The illustration shows schematically how images of a sample block 402 are captured, wherein the sample block 402 has been trimmed obliquely on account of a microtome blade 401 not oriented exactly at right angles relative to the optical axis 403 of the particle-optical apparatus. The sample layer 404 cut off has been discarded. A suitable detector, preferably a BSE detector, is used for capturing the images. Firstly, a first image of the sample is captured, wherein the sample is scanned by the primary particle beam in a raster-type manner and the sample is scanned in a first focal plane 405. A further image of the sample is then captured, wherein the sample is scanned in a further focal plane 406, which differs from the first focal plane 405. The capture of a respective further image of the sample is repeated until an n-th image has been captured with an n-th focal plane 407, wherein the n-th focal plane 407 differs from all preceding focal planes (405, 406). Usually, at least 5 to 10, advantageously 5 to 50, focal planes are captured. All of the captured images are stored. A 3D reconstruction of the sample block is then calculated on the basis of the captured images. The angle $\gamma$ which the primary particle beam running parallel to the optical axis 403 and the normal to the sample surface 408 form relative to one another can be determined on the basis of the 3D reconstruction. The angle between primary particle beam and sample surface can subsequently be corrected, such that the angle is approximately 0°. This can be done by correspondingly moving the sample and/or by correspondingly altering the focal plane of each individual image during the subsequent capture of a series of images. Angle $\gamma$ should be regarded as too large and corrected if angle $\gamma$ is greater than angle $\beta$. Angle $\beta$ is defined as $\beta = D/L$, wherein D denotes the thickness of the sample layer cut off, while L denotes the length of the longitudinal side of the rectangular scanning field scanned by the primary particle beam. It is assumed here that tan β=β, since β assumes only small values because the distance L is usually 10 times greater, preferably 50 times greater, than the distance D. Angle γ is corrected by the sample stage being rotated about a tilting axis of the sample stage until |γ|<|β|.

In principle, when working with a variable focus it is advantageous if the primary particle beam emerges at the highest possible aperture angle α, but this can have a disadvantageous effect on the achievable spatial resolution. Therefore, a compromise should be found between the highest possible aperture angle α and the desired spatial resolution. DOF (depth of field) and FOV (field of view) decrease as the magnification increases. DOF denotes that path segment which runs along the optical axis of the particle-optical apparatus and in which an object must be situated in order that it can be imaged in a focussed manner. FOV is understood to mean that region of the sample which is scanned by the primary particle beam and can be detected by a detector. The following holds true for the relationship between aperture angle α, DOF and magnification Mag:

DOF=line spacing of the display/(Mag*tan α), wherein the line spacing of the display can be 200 μm, for example. The described embodiment of the method according to the invention is particularly suitable for small magnifications, that is to say for magnifications up to approximately 2000 times, preferably up to 1000 times.

Figure 5:
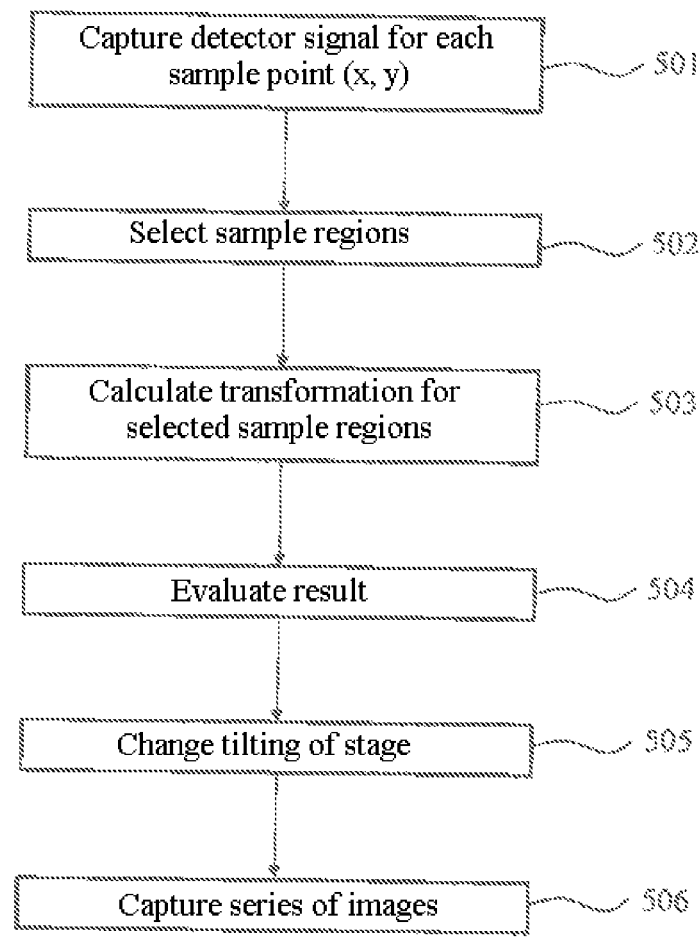

FIG. 5 shows a flowchart of an alternative embodiment of the method according to the invention, by which the angle which the primary particle beam impinging on the sample and the sample surface form relative to one another is determined and can be corrected. For this purpose, images of the sample surface are captured, wherein a defined region of the sample surface is scanned by the primary particle beam. In step 501, the secondary electrons (SE) arising as interaction products are captured as SE signal for each sample point (x, y) in the scanning field, in order to generate an image. In this case, the signal can be detected for example by an in-lens SE detector or an AsB detector (angular selective backscattered electron detector). The AsB detector is a detector which can detect backscattered electrons (BSE) in an angularly selective manner. The detector is usually situated in direct proximity to the objective lens of the particle-optical apparatus and comprises four diodes that can be controlled independently of one another. The next step 502 of the method involves selecting at least three sample regions lying in the outer regions of the captured image. In one advantageous embodiment, exactly three sample regions are selected, but it is also possible to chose five or more sample regions. However, the duration of the subsequent processing also increases with the number of selected sample regions, and so it is not very practical to select significantly more than five sample regions. The selected sample regions span an imaginary plane lying in the plane of the sample surface. The sample regions should be distributed over the entire scanning field scanned by the primary particle beam and should not overlap. It is advantageous, moreover, if the sample is as homogeneous as possible. The size of the selected sample regions should be chosen in a manner dependent on the sample material, for example 30 nm×30 nm. In the case of other samples it may be advantageous to define larger sample regions, such as 100 nm×100 nm, for example. When choosing the size of the sample regions as well it should be taken into consideration that as the size increases, more time is required for the scanning and the subsequent evaluation. The next step 503 involves transforming the image data of the selected sample regions with the aid of a frequency-based computational algorithm. This can be, for example, a Fast Fourier Transformation (FFT) or a Discrete Fourier Transformation (DFT). The transformed data are then evaluated (step 504). The results obtained allow conclusions to be drawn about whether or not the sample region on which the transformation was based was situated in the focus of the imaging components of the particle-optical apparatus: a high spatial frequency in comparison with the average of the spatial frequencies indicates that the sample region is in the focus, while a low spatial frequency in comparison with the average of the spatial frequencies signifies that the sample region is outside the focus. A representation of the spatial frequencies in the reciprocal space is obtained with the aid of the FFT, wherein the observed sample region is represented via concentric circle structures. In this manner of representation, circles near the centre represent low spatial frequencies and thus sample regions lying outside the focus. On the other hand, circles remote from the centre represent high spatial frequencies and thus sample regions in the focus. Since the FFT takes place near-instantaneously, it is possible to make changes in the focus setting at the particle-optical column of the particle-optical apparatus, the effects of which become visible immediately in the FFT representation. In this way, the FFT representations of the at least three sample regions are observed, while focus settings are altered in a targeted manner at the particle-optical apparatus in order to be able to draw conclusions therefrom as to the way in which the tilting angle of the sample has to be altered in order that the impinging incident primary particle beam impinges on the sample surface approximately perpendicularly. This procedure can also be performed in an automated manner. Step 505 then involves correspondingly altering the sample position, such that the angle between the impinging primary particle beam and the sample surface is approximately 90°. The tilting angle of the sample is usually altered for this purpose. Afterwards, step 506 involves capturing images for a series of images with the aid of which the 3D reconstruction of the sample can be created.

Figure 6:
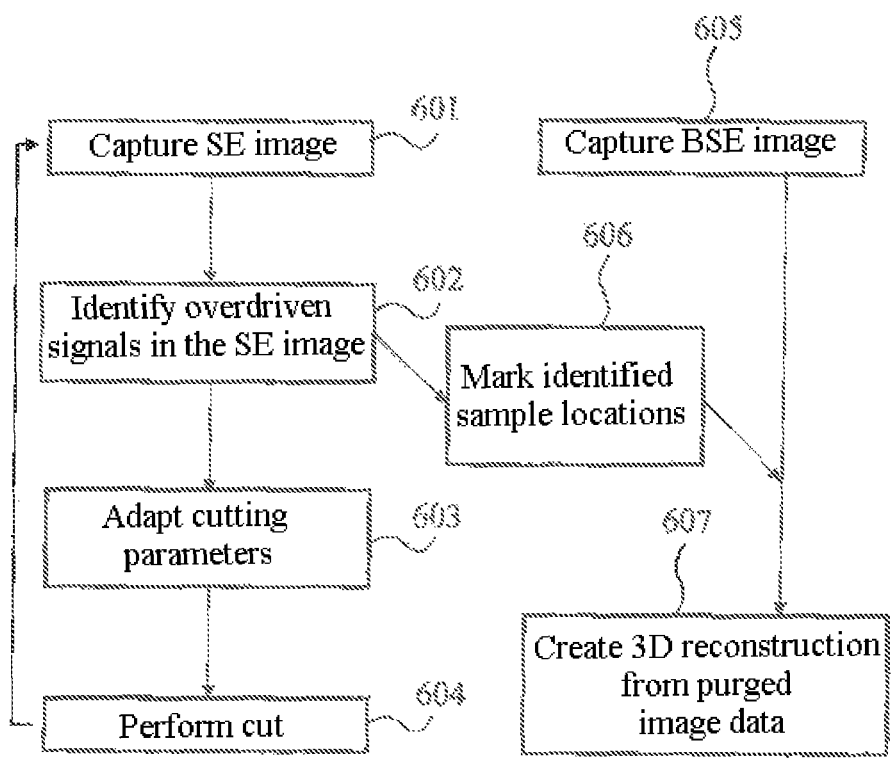

FIG. 6 shows a flowchart of a further specific embodiment of the method according to the invention. Step 601 involves capturing an SE image for each pixel (x, y) of the sample via an SE detector. In one advantageous configuration of the invention, an in-lens SE detector situated within the electron-optical column of the particle-optical apparatus is used for this purpose. At the same time as step 601, a BSE image of the sample is captured in step 605. It has proved to be advantageous to simultaneously record the images of different detectors—of the SE detector and of the BSE detector in this example—with the aid of a plurality of channels. In one particularly advantageous embodiment, the BSE image is captured via a 4QBSE detector (4-quadrant BSE). The 4QBSE detector comprises a ring-shaped detector area subdivided into four segments, the so-called quadrants. The individual quadrants can be driven independently of one another, and the signals detected by each quadrant can be evaluated, taken into account computationally and stored independently of one another. Step 602 involves identifying overdriven or approximately overdriven signals that occur in the SE image, that is to say identifying those pixels which have an overdriven or approximately overdriven SE signal. This can be done by identifying great signal changes during the scanning of the sample with the primary particle beam. On account of the edge effect, interaction products, primarily SE, emerge from the sample material to an increased extent at edge-shaped structures. It is also possible to detect the number of overdriven pixels per sample area. As soon as the number exceeds a specific threshold, this is identified as a conspicuous signal. Via a feedback step 603, the cutting parameters are varied, which means that, for example, cutting speed and/or oscillation frequency and/or oscillation amplitude of the microtome blade are adapted. The aim here is to chose a combination of parameters for which the number of overdriven pixels is as small as possible. With these adapted parameters, in step 604, the sample is then cut, i.e. the outermost sample layer is removed. The next SE image can subsequently be captured according to step 601, in order to check the quality of the cut. Moreover, in the method according to the invention, alternatively or additionally, in step 606, the image data identified in step 602 can be marked during the data processing in such a way that these data are excluded from the 3D reconstruction in step 607, such that the 3D reconstruction is therefore performed only with purged image data.

FIG. 7 shows a flowchart of a further specific embodiment of the method according to the invention, by which the surface roughness of the sample surface can be determined with the aim of reducing the surface roughness of the sample surfaces produced during the subsequent cuts. A first step 701 involves capturing and storing BSE signals for each point (x, y) of the sample surface. This can preferably be done using a 4QBSE detector, the detector area of which is subdivided into four quadrants. The individual quadrants can be driven independently of one another, such that the signals respectively detected can be evaluated, taken into account computationally and stored independently of one another. It is thereby possible to operate the detector both in an operating mode for representing material contrast and in an operating mode for representing topography contrast. The summation signal $s_{x,y}$ determined from the signals of all four quadrants of the 4QBSE detector in step 701 corresponds to the material contrast. In a later step of the method (step 707), these data can be used for creating a 3D reconstruction. In addition, step 701 involves capturing, for each sample point, images which are detected in the operating mode "topography contrast" of the detector and which can be used to determine the height information for each individual sample point. For this purpose, usually at least four images are taken into account computationally with one another in order to obtain, for each sample point (x, y), a height signal $z_{x,y}$ containing the height information of the sample point. The topography of the entire sample surface can be determined from the height signals of the individual points. That means, therefore, that, on the basis of the captured BSE signals, the height information for each point (x, y) can be calculated and stored.

In order to determine the surface roughness, it is customary to compare surface profiles, to be precise in such a way that the vertical deviation of the profile to be examined from a comparative profile (i.e. the profile line of an ideal surface) is determined. In the method according to the invention, therefore, in the subsequent step 703 the surface roughness is determined by determining for the height signals the characteristic variables $R_a$ (arithmetic mean of the absolute values), $R_q$ (rms, root mean square), $R_v$ (minimum peak height), and $R_p$ (maximum peak height).

The following hold true here:

$$R_n = \frac{1}{n}\sum_{i=1}^{n}|y_i|$$

$$R_q = \sqrt{\frac{1}{n}\sum_{i=1}^{n}y_i^2}$$

$$R_v = \min_i y_i$$

$$R_p = \max_i y_i$$

wherein $y_i$ represents the vertical distance between the i-th data point and the corresponding location in the comparative profile of the ideal surface, and n represents the total number of data points.

Desired values of the characteristic variables are defined depending on the sample material. By comparing the characteristic variables determined with the desired values it is possible to decide how the cutting parameters should be adapted. In this regard, by way of example, cutting thickness and/or cutting speed (i.e. delivery of the microtome blade) and/or oscillation parameters of the microtome blade can be adapted. Optimum parameter settings can preferably be determined empirically since the sample material used in each case and current method conditions have to be taken into account. The sample is then cut in step 705. Subsequently, in step 706, steps 701 to 705 are repeated until a sufficient number of cuts m have been carried out and images of m cut planes have been captured. In step 707, a 3D structure of the sample is reconstructed on the basis of the images, wherein conspicuous sample regions are identified. In step 708, a 3D reconstruction is created via the material contrast images captured and stored in steps 701 and 702, wherein the sample regions identified previously do not contribute to the reconstruction. For this purpose, for each sample point (x, y) from each cut plane m, a limit value is defined for $z_{diff}$ for assessing the cut quality. In this case, $z_{diff}$ is defined as: $z_{diff}=z_m-z_{m+1}$, wherein m denotes the number of the cut. $z_{diff}$ can maximally assume the value of the cutting thickness set at the microtome. These image data for which $z_{diff}$ exceeds the limit value are identified and are excluded from the 3D reconstruction. With this embodiment of the method according to the invention it is possible to identify in particular periodically occurring artifacts, for example periodic thickness variations (variations in z).

A further specific embodiment of the invention makes it possible to reduce undesirable electrical charging of the sample block during serial block face imaging. As illustrated in FIG. 1, both the microtome 7 with the microtome blade 8 and the needle 14 of the gas introducing apparatus 12 are arranged in a movable manner within the sample chamber 2. This has the advantage that, despite the spatial restriction within the sample chamber 2, both components can be positioned in direct proximity to the sample, without mutually impeding one another. Both the cutting device, comprising microtome 7 and microtome blade 8, and the needle 14 of the gas introducing apparatus 12 can be situated in two possible positions, namely in a working position or in a rest position; the cutting device (7, 8) and the needle 14 of the gas introducing apparatus 12 can be moved between these two positions. The needle 14 is in direct proximity to the sample in the working position, and at some distance from the sample in the rest position. In the working position of the cutting device, the cutting device (7, 8) is situated so close to the sample that a layer of the sample block 10 can be cut off with the aid of the microtome blade 8. In the rest position, the cutting device (7, 8) is situated so far away from the sample block 10 that a collision with other components of the particle-optical apparatus 1 is precluded. In one particular advantageous embodiment, the microtome blade (8) of the cutting device (7, 8) is a diamond blade.

FIG. 8 illustrates a flowchart of a specific embodiment of the method of the invention. A first step 801 in this embodiment involves preparing a first operating state, in such a way that the needle of the gas introducing apparatus is moved into the working position of the needle and the cutting device is moved into the rest position of the cutting device. The next step 802 involves locally introducing gas at the sample surface, such that the gas is ionized and the charges on the sample surface are compensated for. The gas introduced can be an inert gas, for example nitrogen. As a result of the inert gas being fed in, a locally delimited gas cloud forms at the location where the gas is fed in, preferably in direct proximity to the sample surface. Interaction products, such as SE or BSE, for example, which arise as a result of the interaction of sample material and incident primary particle beam ionize the gas molecules of the gas cloud. The ions that arise in this case, for example positive ions, and electrons are attracted by the charged locations of the sample surface. The ions and/or electrons impinge on the sample and neutralize the surface of the sample. In step 803, one or a plurality of images of the sample are captured via a detector. The subsequent step 804 involves preparing a second operating state by moving the cutting device into the working position of the cutting device and moving the needle into the rest position of the needle. In step 805, a sample layer is then removed by cutting via the cutting device. Finally, in step 806, steps 801 to 805 are repeated until a series of images has arisen. A 3D reconstruction can be created from the series of images.

Besides the embodiments described above, the invention also includes further-reaching aspects which, in particular, need not comprise all the features of the embodiments described above. The invention can for example also be embodied as a method by which the angle which the primary particle beam impinging on the sample and the sample surface form relative to one another can be determined and corrected, wherein the method comprises the following steps:
  a) capturing an image of the sample, wherein the sample is scanned by the primary particle beam in a raster-type manner and the sample is scanned in a first focal plane,
  b) capturing a further image of the sample, wherein the sample is scanned in a further focal plane, which differs from the first focal plane,
  c) repeating step b),
  d) calculating a 3D construction on the basis of the images captured in a) to c),
  e) determining the angle which the primary particle beam and the sample surface form relative to one another, and
  f) correcting the angle between primary particle beam and sample surface, such that the angle is approximately 90°, to be precise by correspondingly moving the sample and/or by correspondingly varying the focal plane of each individual image during the subsequent capture of a series of images.

Furthermore, the invention can be embodied as a method by which the angle which the primary particle beam impinging on the sample and the sample surface form relative to one another can be determined and corrected, wherein the method comprises the following steps:
  a) capturing images of the sample surface, wherein a defined region of the sample surface is scanned by the primary particle beam,
  b) selecting at least three sample regions lying in the outer regions of the captured image,
  c) transforming the image data of the selected sample regions with the aid of a frequency-based computation algorithm,
  d) evaluating the transformed data and determining the focal plane of the sample regions,
  e) varying the sample position in such a way that the angle between the impinging primary particle beam and the sample surface is approximately an angle of 90°.

Furthermore, the invention can be embodied as a method by which cuts not guided exactly can be identified, wherein the method comprises the following steps:
  a) capturing the SE signal for each pixel (x, y) via an SE detector,
  b) identifying pixels having an overdriven or approximately overdriven SE signal,
  c) adapting cutting speed and/or adapting oscillation frequency and/or oscillation amplitude of the microtome blade and cutting the sample with adapted parameters, and/or excluding the image data identified in step b) from the 3D reconstruction.

Furthermore, the invention can be configured as a method by which the surface roughness of the sample surface can be determined and which comprises the following steps:
  a) capturing BSE signals for each point (x, y) of the sample surface via a quadrant detector having at least four quadrants which detect independently of one another,
  c) on the basis of the captured BSE signals, calculating and storing the height information for each point (x, y),
  d) determining the surface roughness,
  e) adapting the cutting parameters and cutting the sample,
  f) repeating steps a) to e),
  g) defining a limit value for assessing the cut quality and excluding those image data which exceed the limit value from the 3D reconstruction.

Finally, the invention can be embodied as a method by which the electrical charging of the sample surface can be reduced or compensated for, wherein the particle-optical apparatus furthermore comprises an apparatus having a movable needle for introducing gas, and the method comprises the following steps:
  a) preparing a first operating state, in such a way that the needle is moved into the working position of the needle and the cutting device is moved into the rest position of the cutting device,
  b) locally introducing gas at the sample surface, in such a way that the gas is ionized and the charges on the sample surface are compensated for,
  c) capturing one or a plurality of images of the sample via a detector,
  d) preparing a second operating state by moving the cutting device into the working position of the cutting device and moving the needle into the rest position of the needle,
  e) removing a sample layer with the aid of the cutting device,
  f) repeating steps a) to e).

In this case, the gas introduced can be nitrogen.

The present invention furthermore relates to a method for compensating for artifacts in a sample during the capture of series of images of the sample via a particle-optical apparatus. In this case, the particle-optical apparatus has at least one particle source which generates a primary particle beam, at least one detector for detecting interaction products which arise during the interaction of primary particle beam and sample, a chamber for accommodating the sample, and a cutting device for removing a surface layer of the sample. In this case, the method comprises the following method steps:

a) capturing a first image of the sample via the detector, wherein the particles of the primary particle beam have a first average energy in such a way that the interaction products detected by the detector predominantly contain sample information from a sample layer lying below the surface layer, b) removing the surface layer of the sample with the aid the cutting device, such that a new surface layer arises, c) capturing a second image of the sample via the detector, wherein the particles of the primary particle beam have a second average energy in such a way that the interaction products detected by the detector predominantly contain sample information from the new surface layer of the sample, d) determining artifacts produced during the removal of the surface layer in the sample by comparing the first and second images, and e) eliminating or compensating for artifacts determined in step d).

In this case, the cutting device can be a microtome or an ultramicrotome having a mechanical blade, a focussed ion beam, a focussed electron beam or a focussed photon beam. In the cases of a focussed ion beam, a focussed electron beam or a focussed photon beam, a gas feed device can additionally be present in order to feed to the sample a process gas which can be activated by the focussed beam or interaction products of the focussed beam of the sample. In this case, the artifacts produced during the removal of the surface layer of the sample can be—introduced into the sample—(implanted) ions of the ion beam, atoms of the process gas or changes in the sample produced by the energy action of the focussed beam in the sample. The artifacts can be compensated for by a procedure in which sample locations at which the sample material was not sufficiently removed are reworked in order additionally to remove sample material. On the other hand, it is possible to identify sample locations at which too much material was removed. Such sample locations can be assigned to a different sample layer during the 3D reconstruction or can be completely excluded from the 3D reconstruction.

LIST OF REFERENCE SIGNS

1 Particle-optical apparatus
2 Sample chamber
3 Electron-optical column
4 Primary particle beam
5 First detector
6 Interaction products
7 Microtome
8 Microtome blade
9 Sample stage
10 Sample block
12 Gas introducing apparatus
13 Evaluation and control unit
14 Needle
15 Optical axis
201 Step: Capturing a first image with a first acceleration voltage
202 Step: Removing the outermost sample layer
203 Step: Capturing a second image with a second acceleration voltage
204 Step: Comparing the first and second images
205 Step: Compensating for the lateral offset
301 First sample detail
301a First sample detail after cutting
302 Second sample detail
302a Second sample detail after cutting
303 First sample surface
303a Second sample surface
304 Imaged sample layer
305 First image of the sample
305a Second image of the sample
306 Outermost sample layer
307 Cutting line of the microtome cut
401 Microtome blade
402 Sample block
403 Optical axis
404 Sample layer cut off
405 First focal plane
406 Second focal plane
407 n-th focal plane
408 Sample surface
501 Step: Capture detector signal for each sample point
502 Step: Select sample regions
503 Step: Carry out transformation for selected sample points
504 Step: Evaluate results
505 Step: Change tilting of stage
506 Step: Capture series of images
601 Step: Capture SE image
602 Step: Identify overdriven signals in the SE image
603 Step: Adapt cutting parameters
604 Step: Perform cut
605 Step: Capture BSE image
606 Step: Mark identified sample locations
607 Step: Create 3D reconstruction from purged image data
701 Step: Capture BSE signals
702 Step: Store z and s separately
703 Step: Calculate characteristic variables for s
704 Step: Adapt cutting parameters
705 Step: Perform cut
706 Step: Repeat steps 701 to 705
707 Step: Reconstruct 3D structure and identify conspicuous sample regions
708 Step: Eliminate identified sample regions from the reconstruction
801 Step: Prepare first operating state
802 Step: Locally introduce gas
803 Step: Capture image of the sample
804 Step: Prepare second operating state
805 Step: Cut sample layer
806 Step: Repeat steps 801 to 805

The invention claimed is:

1. A method, comprising:

a) obtaining a first image of a sample based on detected interaction products of a first primary particle beam and the sample, the particles of the first primary particle beam having a first average energy so that the detected interaction products predominantly contain sample information for a sample layer which is a sub-surface layer of the sample lying below a surface layer of the sample;

b) after a), removing the surface layer of the sample via a cutting device to provide a new surface layer of the sample which corresponds to the sub-surface layer in a);

c) after b), exposing the sample to a second primary particle beam generated by the particle source;

d) after c), obtaining a second image of the sample based on detected interaction products of a second primary particle beam and the sample, the particles of the second primary particle beam having a second average energy so that the detected interaction products predominantly contain sample information for the new surface layer of the sample corresponding to the sub-surface layer in a); and e) after d), calculating a lateral shift of the sample based on a comparison of the first and second images, wherein the first and the second image predominately contain sample information for the same sample layer.

2. The method of claim 1, further comprising compensating for the lateral shift.

3. The method of claim 1, wherein the interaction products detected in a) and d) comprise primary particles scattered at the sample detected via a BSE detector.

4. The method of claim 1, wherein the first average energy is greater than the second average energy.

5. The method of claim 1, wherein the first average energy is greater than 2 keV.

6. The method of claim 5, wherein the second average energy of the particle beam is less than 2 keV.

7. The method of claim 1, wherein the second average energy of the particle beam is less than 2 keV.

8. The method of claim 1, wherein the first image of the sample contains information from a sample layer which lies 10 nm to 50 nm below the surface of the sample.

9. The method of claim 1, further comprising moving the sample to compensate for the lateral shift.

10. The method of claim 1, further comprising deflecting a primary particle beam to compensate for the lateral shift via a shift of the scanned scanning field.

11. The method of claim 1, comprising compensating for the lateral shift via computational methods during 3D reconstruction after obtaining a series of images of the sample.

12. The method of claim 1, wherein e) comprises cross-correlating the first and second images.

13. The method of claim 1, further comprising:
1) scanning a primary particle beam across the sample while the sample is in a first focal plane to obtain an image of the sample;
2) scanning a primary particle beam across the sample while the sample is in a second plane to obtain an image of the sample, the second focal plane being different from the first focal plane,
3) repeating 2);
4) calculating a 3D construction on the basis of the images obtained in 1) through 3),
5) determining an angle which the primary particle beam and the sample surface form relative to one another; and
6) adjusting the angle between primary particle beam and sample surface so that said angle is approximately 90°.

14. The method of claim 13, wherein 6) comprises moving the sample and/or varying the focal plane of each individual image during the subsequent attainment of a series of images.

15. The method of claim 1, further comprising:
1) obtaining images of the sample surface, a defined region of the sample surface being scanned by the primary beam;
2) selecting at least three sample regions lying in the outer regions of the obtained image;
3) transforming the image data of the selected sample regions via a frequency-based computation algorithm;
4) evaluating the transformed data and determining the focal plane of the sample regions; and 5) varying the sample position so that an angle between the primary particle beam and the sample surface is approximately an angle of 90°.

16. The method of claim 1, further comprising:
1) for each point of the sample surface, obtaining a signal of primary particles scattered at the sample surface via a quadrant detector having at least four quadrants which detect independently of one another;
2) on the basis of the obtained signals, calculating and storing the height information for each point on the sample surface;
3) determining a surface roughness;
4) adapting the cutting parameters and cutting the sample;
5) repeating 1) through 4); and
6) defining a limit value for assessing the cut quality and excluding those image data which exceed the limit value from the 3D reconstruction.

17. The method of claim 1, further comprising:
1) preparing a first operating state so that a needle is moved into a working position of the needle and the cutting device is moved into a rest position of the cutting device;
2) locally introducing gas at the sample surface via the needle so that the gas is ionized and the charges on the sample surface are compensated for;
3) obtaining at least one image of the sample via the detector;
4) preparing a second operating state by moving the cutting device into its working position and moving the needle into a rest position of the needle; and
5) removing a sample layer with the aid of the cutting device.

18. The method of claim 17, wherein the gas comprises nitrogen.

19. The method of claim 1, wherein the cutting device comprises a blade.

20. The method of claim 19, wherein the blade of the cutting device comprises a diamond blade.

21. The method of claim 19, further comprising:
1) for each point of the sample surface, using a SE detector to obtain a signal of secondary electrons released from the sample due to an interaction of the primary particle beam with the sample;
2) identifying pixels having an overdriven or approximately overdriven output signal of the SE detector; and
3) adapting cutting speed and/or adapting oscillation frequency and/or oscillation amplitude of the blade and cutting the sample with adapted parameters, and/or excluding the image data identified in 2) from the 3D reconstruction.

22. The method of claim 1, wherein the first average energy is the average energy of all the particles of the first primary particle beam, and the second average energy is the average energy of all the particles of the second primary particle beam.

23. A method, comprising:
a) detecting interaction products of a first primary particle beam and a sample to obtain a first image of a first layer of the sample while the first layer of the sample is a sub-surface layer of the sample which lies below an exposed surface of the sample;
b) after a), removing a portion of the sample so that the first layer of the sample is an exposed layer of the sample;
c) after b), detecting interaction products of a second primary particle beam and the sample to obtain a second image of the first layer of the sample while the first layer is the exposed layer of the sample; and d) after c), calculating a lateral shift of the sample based on a comparison of the first and second images of the first layer, wherein the first and second images are both images of the first layer.

24. A method, comprising:

a) obtaining a first image of a sample based on detected interaction products of a first primary particle beam and the sample, the particles of the first primary particle beam having a first average energy so that the detected interaction products predominantly contain sample information for a first layer of the sample, the first layer of the sample being a sub-surface layer of the sample lying below a surface layer of the sample;

b) after a), removing the surface layer of the sample via a cutting device to provide a new surface layer of the sample, the new surface layer of the sample being the same as the first layer of the sample;

c) after b), exposing the sample to a second primary particle beam generated by the particle source;

d) after c), obtaining a second image of the sample based on detected interaction products of a second primary particle beam and the sample, the particles of the second primary particle beam having a second average energy so that the detected interaction products predominantly contain sample information for the first surface layer of the sample; and e) after d), calculating a lateral shift of the sample based on a comparison of the first and second images.

* * * * *

UNITED STATES PATENT AND TRADEMARK OFFICE
CERTIFICATE OF CORRECTION

| | |
|---|---|
| PATENT NO. | : 9,536,704 B2 |
| APPLICATION NO. | : 14/021075 |
| DATED | : January 3, 2017 |
| INVENTOR(S) | : Matthias Langer et al. |

It is certified that error appears in the above-identified patent and that said Letters Patent is hereby corrected as shown below:

On the Title Page

Item (54) and in the Specification, Column 1, Line 1, delete "ARTEFACTS" and insert -- ARTIFACTS --.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*